United States Patent [19]

Melby

[11] 4,292,212
[45] Sep. 29, 1981

[54] SHAMPOO CREME RINSE

[75] Inventor: Allan L. Melby, Andover, Minn.

[73] Assignee: Henkel Corporation, Minneapolis, Minn.

[21] Appl. No.: 964,567

[22] Filed: Nov. 29, 1978

[51] Int. Cl.$^3$ .................. A61K 7/08; C11D 1/88; C11D 1/94; C11D 3/37

[52] U.S. Cl. .................. 252/547; 252/142; 252/145; 252/153; 252/154; 252/155; 252/173; 252/174.23; 252/542; 252/545; 252/546; 252/550; 252/DIG. 2; 252/DIG. 5; 252/DIG. 13; 424/70; 424/78; 536/114

[58] Field of Search .............. 252/153, 154, 155, 142, 252/144, 145, 173, 174.23, 524, 528, 542, 547, 546, 550, DIG. 2, DIG. 5, DIG. 7, DIG. 13; 424/70, 71, 78; 536/114

[56] References Cited

U.S. PATENT DOCUMENTS 3,589,978   6/1971   Kamal ............................ 162/158
4,061,602  12/1977   Oberstar et al. ............... 424/70 X Primary Examiner—Dennis L. Albrecht
Attorney, Agent, or Firm—Forrest L. Collins; Patrick J. Span

[57] ABSTRACT

A shampoo-creme rinse composition for improving the combing properties and luster of hair which comprises a single phase aqueous detergent composition containing an amphoteric detergent and an anionic detergent and a cationic derivative of a 3-(trimethylamino)-2-hydroxypropyl guar chloride salt.

1 Claim, No Drawings

SHAMPOO CREME RINSE

CROSS REFERENCE

Claims to the present invention have also been made in U.S. Pat. No. 4,061,602 issued to Oberstar et al. on Dec. 6, 1977.

BACKGROUND OF THE INVENTION

The present invention relates to a unitary shampoo-creme rinse composition for improving the combing properties, manageability, and luster of hair which comprises a single phase aqueous detergent composition containing an amphoteric detergent and an anionic detergent and a cationic derivative of a 3-(trimethylamino)-2-hydroxypropyl guar chloride salt.

The possibility of combining shampoo action with creme rinse and conditioning action in a single composition for use in a single treatment of hair has been previously investigated. It is known that anionic detergents and polymers are suitable for shampooing and that cationic detergents and polymers are useful as creme rinses. The combination of an anionic detergent and a cationic detergent was considered difficult because of inherent incompatibility. It has recently been discovered, however, that anionic detergents are compatible with certain types of cationic polymers and that effective hair conditioning shampoo compositions can be obtained thereby. Throughout the specification and claims percentages and ratios are by weight and temperature are in Celsius unless otherwise indicated.

DETAILED DESCRIPTION OF THE INVENTION

It has now been discovered that improved combing properties, improved hair conditioning and observable highly desirable shine or luster can be imparted to hair by shampoo compositions which contain the proper proportions of an amphoteric and anionic surface active agent and a cationic derivative of a 3-(trimethylamino) -2-hydroxypropyl guar chloride salt. The particle size of the 3-(trimethylamino)-2-hydroxypropyl guar chloride salt is also important in preparing a product having these desirable qualities.

The cationic derivatives of 3-(trimethylamino)-2-hydroxypropyl guar chloride salt which are useful in combination with anionic and amphoteric surface active agents are quaternary ammonium salts as described in U.S. Pat. No. 3,589,978 to Kamal et al. issued June 29, 1971 and assigned to General Mills Chemicals, Inc.

The materials of Kamal et al. contain as the basic unit two mannose units with a glycosidic linkage and a galactose unit attached to one of the hydroxyls of the mannose units. On the average, each of the sugar units has three available hydroxyl sites. The hydroxyl groups of the guar are reacted with certain reactive quaternary ammonium compounds to produce the cationic polymers of the present invention. Various polymers can be obtained thereby depending on the quaternary ammonium compound used and on the degree of substitution (D.S.), up to a maximum of three per sugar unit. The quaternary ammonium compounds are available commercially as Cosmedia ® C-261 cationic guar. The cationic guar preferably has a particle size distribution such that 69% by weight of the particles are 45 microns or smaller and 98% by weight of the particles are 105 microns or smaller thereby providing a product of greater clarity. The finer particles have a faster hydration rate in preparing an aqueous product of this invention.

The cationic portion of the compounds which are suitable for preparing the polymers of the invention are defined as conforming to the structure:

The full formula for the guar derivative of the 3-chloro-2-hydroxypropyl trimethyl ammonium chloride is:

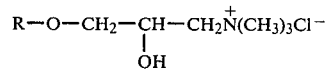

where R represents the guar molecule.

The shampoo-creme rinse composition of the present invention contains a mixture of one or more amphoteric detergents and one or more anionic detergents, generally in essentially equal amounts, although their relative proportions may vary widely.

Suitable amphoteric detergents include fatty alkyl dicarboxylic derivatives of imidazolines, such as those sold as Miranols; alkyl beta-aminopropionates, such as Deriphat ® amphoteric surfactant, sold by General Mills Chemical, Inc.; sultaines, such as 1-(myristyl dimethylammonio)-2-hydroxypropane- 3-sulfonate, and betaines, such as 1-(myristyl dimethylammonio) acetate, and the like. A preferred amphoteric detergent is the dicarboxylic coconut derivative sold under the name Miranol C2M-SF. The proportion of amphoteric detergent used in the shampoo composition should be sufficient to produce the desired effect of solubilizing the cationic polymer and providing a vehicle for deposition on the hair, but ordinarily will range between 5 and 20 percent by weight, preferably 7 to 17 percent by weight most preferably 10 percent by weight.

Anionic detergents are generally added to the shampoo composition to provide foaming and also to solubilize the polymer. Suitable anionic detergents include sodium lauryl sulfate particularly Standapol ® ES40 anionic surfactant available from Henkel, Inc., sodium polyhydroxy monoether sulfate, cocoyl sarcosine, diethanol/triethanol ammonium lauryl sulfate, triethanolamine laureth (lauryl ether) sulfate and the like. A preferred anionic detergent is cocoyl sarcosine sold under the trade name Hamposyl C. The anionic detergent is used in an amount ranging from about 5 to 20 percent by weight, preferably 7 to 17 percent by weight more preferably 10% by weight.

Suitable nonionic detergents, which provide rinsability and wet and dry conditioning, include polyethylene glycol mono- and distearates, octyl and nonylphenoxy polyethoxyethanol, such as Triton X-100, fatty acid alkanolamides, oxyethylated polypropylene glycols, such as Pluronics (BASF Wyandotte), amine oxides, and the like. A particularly preferred nonionic is polyethylene glycol 6000 distearate, sold by Armak Co. The nonionic detergent may be used in an amount ranging from about 0.1 to 5 percent by weight, preferably 0.1 to 1 percent by weight.

The cationic polymer is used in amount sufficient to impart conditioning action to the hair, but ordinarily is used in an amount of from about 0.1 to 5 percent by weight, preferably 0.2 to 2 percent by weight.

The pH of the composition should be at least about 4.5, to about 8.0, and desirably from about 5.5 to 7.5. The pH may be adjusted to the desired level by the use of an acidic and/or an alkaline material, for example citric acid or water-soluble amines such as triethanolamine. Citric acid also serves as a sequestering agent and a buffering agent and is frequently added for these purposes even if not needed for pH adjustment.

Various other additives are conventionally added to shampoo compositions such as perservatives, dyes, perfumes, antibacterials, anti-dandruff ingredients, and the like.

The following specific example is illustrative of the invention, and will enable persons skilled in the art to better understand and practice the invention.

EXAMPLE 1

|  | % by Weight Solids |
|---|---|
| Deriphat ® 160C amphoteric surfactant | 10% |
| Standapol ® ES-40 anionic surfactant | 10% |
| Cationic guar (previously described) | 0.5% |
| Balance Water | |

The above formulation is evaluated for both wet and dry hair properties for shampoo and creme rinse properties and performs well.

A second example is done by substituting the finer particle size Cosmedia ® C-261 cationic guar with even more striking results in the clarity of the aqueous product.

We claim:

1. A shampoo-creme rinse composition comprising about 5 to 20 weight percent of at least one amphoteric detergent, about 5 to 20 weight percent of at least one anionic detergent and from about 0.1 to 5 weight percent of 3-(trimethylamino)-2-hydroxypropyl guar chloride salt wherein the guar chloride salt is derived from particulate guar wherein 69% by weight of the particles are 45 microns or smaller and 98% by weight of the particles are 105 microns or smaller.

* * * * *